(12) United States Patent
Shi et al.

(10) Patent No.: US 11,467,141 B2
(45) Date of Patent: Oct. 11, 2022

(54) MARKER PEPTIDE OF SNAKE VENOM THROMBIN-LIKE ENZYMES (SVTLES) FROM AGKISTRODON HALYS PALLAS AND APPLICATION THEREOF

(71) Applicants: Shandong Institute for Food and Drug Control, Shandong (CN); Shandong University, Shandong (CN); Avanc Pharmaceutical Co., Ltd, Liaoning (CN)

(72) Inventors: Feng Shi, Shandong (CN); Ruiqing Xian, Shandong (CN); Liping Gong, Shandong (CN); Weijian Wang, Shandong (CN); Lianli Chi, Shandong (CN); Congcong Wang, Shandong (CN); Baojian Hang, Shandong (CN); Xunjie Zhang, Shandong (CN); Li Nie, Liaoning (CN); Fengshan Wang, Shandong (CN)

(73) Assignees: Shandong Institute for Food and Drug Control, Shandong (CN); Shandong University, Shandong (CN); Avanc Pharmaceutical Co., Ltd, Liaoning (CN)

( * ) Notice: Subject to any disclaimer, the term of this patent is extended or adjusted under 35 U.S.C. 154(b) by 0 days.

(21) Appl. No.: 17/389,322

(22) Filed: Jul. 29, 2021

(65) Prior Publication Data
US 2022/0034856 A1   Feb. 3, 2022

(30) Foreign Application Priority Data
Jul. 30, 2020 (CN) .......................... 202010752988.2

(51) Int. Cl.
*G01N 30/88* (2006.01)
*G01N 30/72* (2006.01)
*G01N 30/96* (2006.01)

(52) U.S. Cl.
CPC ............. *G01N 30/88* (2013.01); *G01N 30/72* (2013.01); *G01N 30/96* (2013.01); *G01N 2030/8831* (2013.01)

(58) Field of Classification Search
CPC .................... G01N 2030/8831; G01N 30/88
See application file for complete search history.

(56) References Cited

U.S. PATENT DOCUMENTS

| 6,291,247 B1 * | 9/2001 | Riopelle ................ G01N 33/74 436/2 |
| 2002/0064517 A1 * | 5/2002 | Cederholm-Williams .................. A61K 48/0041 435/325 |

* cited by examiner

*Primary Examiner* — Lisa M Caputo
*Assistant Examiner* — Alex T Devito
(74) *Attorney, Agent, or Firm* — JCIP Global Inc.

(57) ABSTRACT

The present invention relates to the field of chemical analysis detection and application, in particular to a marker peptide of snake venom thrombin-like enzymes (SVTLEs) from *Agkistrodon Halys Pallas* and an application thereof. The amino acid sequence of the marker peptide of snake venom thrombin-like enzymes (SVTLEs) from *Agkistrodon Halys Pallas* is TLCAGVMEGGIDTCNR. Characterizing the source of species and a content of the SVTLEs in a to-be-detected sample by using the marker peptide includes the following steps of: pretreating the to-be-detected sample by trypsin through enzymolysis, and taking a supernatant of an enzymolysis liquid as a test solution; and injecting the test solution and a reference solution into a liquid chromatography-mass spectrometer, and selecting a qualitative ion pair and a quantitative ion pair for detecting the source of species and a content of the SVTLEs in the to-be-detected sample.

11 Claims, 5 Drawing Sheets

Specification includes a Sequence Listing.

MARKER PEPTIDE OF SNAKE VENOM THROMBIN-LIKE ENZYMES (SVTLES) FROM AGKISTRODON HALYS PALLAS AND APPLICATION THEREOF

CROSS-REFERENCE TO RELATED APPLICATION

This application claims the priority benefit of China application serial no. 202010752988.2, filed on Jul. 30, 2020. The entirety of the above-mentioned patent application is hereby incorporated by reference herein and made a part of this specification.

BACKGROUND

Technical Field

The present invention relates to the field of chemical analysis detection and application, in particular to a marker peptide of snake venom thrombin-like enzymes (SVTLEs) from *Agkistrodon Halys Pallas* and an application thereof.

Description of Related Art

As unique snake species in China, *Agkistrodon Halys Pallas* is mainly distributed in Changbai Mountain Area in the northeast and is also called as the subspecies of *Agkistrodon Halys Pallas*. Snake venom thrombin extracted from the venom of *Agkistrodon Halys Pallas* is serine protease having the arginine esterase activity and the amido enzyme activity, may play a key role during coagulation and is called as "thrombin-like enzyme" due to the similar structure and function with human thrombin-like enzyme. The snake venom thrombin is mainly clinically used for treating hemorrhagic diseases, especially bleeding of blood capillaries and may significantly shorten the bleeding time and reduce the bleeding volume of a patient. The snake venom thrombin becomes a main choice for clinicians in treatment of hemorrhagic diseases as having the advantages of being effective, quick-acting, long-effective, convenient, safe, resistant to a thrombin inhibitor and the like. Currently, the snake venom thrombin products on the market in China are mainly originated from *Bothrops atrox, Deinagkistrodon acutus, Vipera russelli siamensis* and *Agkistrodon Halys Pallas*. Since the thrombin-like enzyme originated from different snake species is different in structure, differences can be found in the mechanism of action and corresponding pharmacological action, and it is of great significance of establishing a strong-specificity and high-sensitivity method to characterize the source of species and the content for control on the quality of snake venom thrombin products.

Venom is a complex mixture secreted by poison gland of snakes and contains various proteins, polypeptide, nucleoside, enzymes, metal ions and other small molecules. The venom may be one of the most complicated substances among all poisons in nature, containing trace amount of over 50 kinds of proteolytic enzyme. There is no control on the source of species in the current quality standard of *Agkistrodon Halys Pallas* venom and no method for specifically detecting a content of thrombin-like enzyme. The currently reported methods for characterizing the content of snake venom thrombin-like enzymes (SVTLEs) mainly include pulsed field gel electrophoresis and an efficacy testing method. Such determination methods are complicated and are poor in accuracy so as not to accurately characterize the mass of the venom. In this regard, establishment of a convenient and rapid qualitative and quantitative method for accurately quantifying the SVTLEs from *Agkistrodon Halys Pallas* has extensive social benefit and economic effect.

SUMMARY

In order to overcome the defects in the prior art, the present invention provides marker peptide of snake venom thrombin-like enzymes (SVTLEs) from *Agkistrodon Halys Pallas* and the technical application of the marker peptide in characterizing the source of species and a content of SVTLEs in a to-be-detected sample. This technical method is simple and convenient, is accurate in quantification, fills the gap in the quality standard for venom of *Agkistrodon Halys Pallas* and improves the quality control level.

To achieve the above inventive objective, the present invention employs the following technical solution:

provided is the marker peptide for the SVTLEs from *Agkistrodon Halys Pallas*, an amino acid sequence of which is TLCAGVMEGGIDTCNR.

Further, provided is the application of the marker peptide for the SVTLEs from *Agkistrodon Halys Pallas*, in which the aforesaid marker peptide is use to detect the source of species and/or the content of the SVTLEs in the to-be-detected sample; and the application includes the following steps:

(1) pretreating the to-be-detected sample by trypsin through enzymolysis, and taking a supernatant of an enzymolysis liquid as a test solution;

(2) pretreating a reference substance of the marker peptide of snake venom from *Agkistrodon Halys Pallas* by the trypsin through enzymolysis, and preparing a series of reference solutions with different concentrations;

(3) injecting the test solution in the step (1) and the reference solution in the step (2) into a liquid chromatography-mass spectrometer, conducting multiple-reaction monitoring by employing an electrospray positive ion mode with double charges 877.4→550.2 (in mass to charge (m/z) ratio) as a qualitative ion pair and double charges 877.4→892.4 as a quantitative ion pair;

(4) in an extracted test solution ion chromatograms (XIC) of the qualitative ion pair and the quantitative ion pair in the step (3), if showing a chromatographic peak with a the chromatographic retention time consistent with that of a reference marker peptide, showing that the to-be-detected sample includes an amino acid sequence of TLCAGVMEGGIDTCNR, proving that the to-be-detected sample is originated from *Agkistrodon Halys Pallas*, or otherwise proving that the to-be-detected sample is not originated from *Agkistrodon Halys Pallas*; and;

(5) extracting the double-charge 877.4→892.4 chromatogram of the ion pairs, calculating a linear regression equation with a concentration of the marker peptide in the series of standard reference solutions as a horizontal coordinate and a corresponding peak area as a vertical coordinate (r>0.99), calculating a concentration of the test solution through the regression equation, and then calculating a content of thrombin-like enzyme in the to-be-detected sample.

Further, the limit of detection and the limit of quantification of the marker peptide for the snake venom from *Agkistrodon Halys Pallas* are 2 ng/mL and 6 ng/mL respectively.

Further, the pretreating with the trypsin through enzymolysis in the step (1) includes the following specific operation steps of: putting 20 mg of the to-be-detected sample in a 10 mL measuring flask, and dissolving the to-be-detected sample with 25 mmol/L ammonium bicarbonate solution to a constant volume; measuring 200 μL of a product, adding 10 μL of a 0.2 mol/L dithiothreitol solution, conducting uniform mixing, conducting reaction for 60 min at 60° C., adding 20 μL of a 0.2 mol/L iodoacetamide solution, conducting reaction in the dark for 30 min, adding 760 μL of 25 mmol/L ammonium bicarbonate solution, and 10 μL of a 0.4 mg/mL trypsin solution for enzymolysis for 90 min at 37° C., conducting inactivation for 10 min at 90° C., cooling to a room temperature, and conducting centrifugation for 10 min at 1200 rpm to obtain the supernatant.

Further, the pretreating with the trypsin through enzymolysis in the step (2) includes the following specific operation steps of: precisely weighing 10 mg of a reference substance of the marker peptide, putting the reference substance of the marker peptide in a 100 mL measuring flask, dissolving the reference substance of the marker peptide with 25 mmol/L ammonium bicarbonate solution, diluting the reference substance of the marker peptide to the scale, conducting uniform shaking, precisely weighing 0.1 mL, 0.25 mL, 0.5 mL, 1 mL, 2 mL of a mixture to be put in 100 mL measuring flasks respectively, dissolving the mixtures with the 25 mmol/L ammonium bicarbonate solution, diluting the mixtures to the scale, and conducting uniform shaking; and adding 10 μL of a 0.2 mol/L dithiothreitol solution 200 μL of a product, conducting uniform mixing for reaction for 60 min at 60° C., adding 20 μL of a 0.2 mol/L iodoacetamide solution in another 200 μL of the product for reaction for 30 min in the dark, adding 760 μL of the 25 mmol/L ammonium bicarbonate solution and 10 μL of a 0.4 mg/mL trypsin solution in another 200 μL of the products for enzymolysis for 90 min at 37° C. and inactivation for 10 min at 90° C. respectively, cooling to the room temperature, and conducting centrifugation for 10 min at 1200 rpm to obtain supernatants.

Further, the liquid phase conditions and the mass spectrum conditions in the liquid chromatogram-mass spectrometer are as follows:

liquid phase conditions: Waters ACQUITY UPLC BEH $C_{18}$ column, 50 mm×2.1 mm, 1.7 μm particle size; a column temperature is 40° C.; the sample size is 2 μL; the flow rate is 0.2 mL/min; a mobile phase A is 0.1% formic acid solution, and a mobile phase B is 0.1% formic acid acetonitrile for gradient elution, wherein the elution program: 0→1 min, mobile phase A: 80%; 1→5 min, mobile phase A 80%→10%; and 5→7 min, mobile phase A 10%→10%.

Mass spectrum conditions: ESI source, positive ion scanning mode, multiple-reaction monitoring; vortex ion spraying temperature: 500° C.; ionization potential: 5.5 kV; outlet voltage of a collision chamber: 10 V; inlet voltage EP: 10 V; collision energy CE: 45 V, declustering potential DP: 135 V.

In the above method, the to-be-detected sample is the snake venom.

Beneficial Effect of the Invention (1) a marker peptide fragment (TLCAGVMEGGIDTCNR) of the SVTLEs from *Agkistrodon Halys Pallas* has been found based on lots of experimental studies and protein database comparisons. Since it has been known that an amino acid sequence of this fragment is not included in the amino acid sequence of the SVTLEs in *Bothrops atrox, Vipera russelli siamensis* and *Deinagkistrodon acutus*, the marker peptide may be used for detecting the source of species and the content of the SVTLEs in the to-be-detected sample.

(2) The qualitative and quantitative method disclosed in the present invention is simple, convenient and rapid, is accurate in quantification, fills the gap in the quality standard for the venom of *Agkistrodon Halys Pallas*, and improving the quality control level of *Agkistrodon Halys Pallas* venom, may greatly increase the quality control level of the venom of *Agkistrodon Halys Pallas* and ensures the effectiveness and the safety of SVTLEs products of *Agkistrodon Halys Pallas* for clinical medication.

DESCRIPTION OF THE EMBODIMENTS

The present invention will be further described below in combination with specific embodiments:

Preparation methods for relevant reagents and solutions in following embodiments are as shown below:

(1) Reagent: trypsin (Sigma, Batch No.: SLBS8956), SVTLEs from *Agkistrodon Halys Pallas* (Avanc Pharmaceutical Co., Ltd., Purity: 98.5%), guanidine hydrochloride (VETEC, Batch No.: WXBC4261V), tromethamine (Shanghai, Batch No.: 20181206), dithiothreitol (BBI Life Sciences, Batch No.: D911BA0011), iodoacetamide (BBI Life Sciences, Batch No.: B326BA1943), while other reagents are all analytically pure.

(2) 25 mmol/L ammonium bicarbonate solution: weighing 79.06 mg of ammonium bicarbonate, and then dissolving the ammonium bicarbonate with 40 mL of water to obtain the solution.

(3) Dithiothreitol (DTT) solution: weighing 15.42 mg of dithiothreitol, and then dissolving the dithiothreitol with 500 μL of water to obtain the solution.

(4) Iodoacetamide (IA) solution (which is newly prepared upon use): weighing 18.5 mg of iodoacetamide, and then dissolving the iodoacetamide with 500 μL of water to obtain the solution.

(5) 0.4 mg/mL trypsin solution (which is newly prepared upon use): weighing 8.0 mg of trypsin, and then dissolving the trypsin with 20 mL of water to obtain the solution.

Embodiment 1

Screening and confirmation of marker peptide for SVTLEs from *Agkistrodon Halys Pallas*.

1. Instrument and Equipment

Thermo Fusion high resolution mass spectrometer (Thermo Fisher Scientific, America), EASY-nLC 1000 nL Nanoliter liquid chromatograph (Thermo Fisher Scientific, America), CP225D electronic scales (Sartorius, Germany), Sigma 3-30 K refrigerated centrifuge (Sigma, Germany), Millipore Milli-QAdvantage A10 Ultra-Pure Water Purifier (Millipore, America)

2 LC-MS/MS Analysis

Chromatographic column: desalting and enrichment were conducted by using a 0.2 mm×3.5 cm (5 μm partical size)

ReproSil-Pur $C_{18}$-AQ Trap column made in the laboratory, and a 75 μm×25 cm (3 μm partical size) ReproSil-Pur $C_{18}$-AQ nanoliter analytical column made in the laboratory was employed for separation. A mobile phase A is a 0.1% formic acid solution of 2% acetonitrile, while a mobile phase B is a 0.10% formic acid solution of 98% acetonitrile. The flow rate of a nanoliter separation pump is 300 nL/min, and gradient elution settings are as shown in Table 1 below.

TABLE 1

List of Gradient Elution for Nanoliter Liquid Phase-High Resolution Mass Spectrum

| Time (min) | Mobile Phase A (nL/min) | Mobile Phase B (nL/min) |
|---|---|---|
| 0 | 300 | 0 |
| 3 | 300 | 0 |
| 5 | 300 | 0 |
| 20 | 270 | 30 |
| 75 | 204 | 96 |
| 95 | 150 | 150 |
| 100 | 0 | 300 |
| 100.5 | 0 | 450 |
| 108 | 0 | 450 |
| 110 | 450 | 0 |
| 115 | 450 | 0 |
| 120 | 450 | 0 |

Mass spectrum conditions: a positive ion mode was employed for analysis, wherein the spray voltage was 2.0 kV, a temperature of an ion transport capillary was 275° C., and the transmission efficiency of S-Lens was set as 60%. Orbitrap was taken as a mass analyzer for a primary mass spectrum, wherein a resolution ratio was 60000, and a collection scope was 350-1650. IT was taken as the mass analyzer for a secondary mass spectrum, and a Rapid Scan mode was employed for scanning, a Top20 data dependence mode is employed for parent ion selection, and an HCD mode was employed for fracturing, the normalized collision energy (NCE) was set as 35%.

3. Data Collection 5 mg of SVTLE from *Agkistrodon Halys Pallas* was put in a 10 mL measuring flask and was dissolved with 25 mmol/L ammonium bicarbonate solution to a constant volume; 200 μL of the solution was precisely measured, 200 μL of a 0.2 mol/L dithiothreitol solution was added, a mixture was blended uniformly and reacted for 1 h at 60° C., 20 μL of a 0.2 mol/L iodoacetamide solution was added, a mixture was placed in the dark for 30 min, 760 μL of the 25 mmol/L ammonium bicarbonate solution and 10 μL of a 0.4 mg/mL trypsin solution (which was newly prepared upon use) were added, the mixture was reacted for 90 min at 37° C. and inactivated for 10 min at 90° C., then cooled to a room temperature, and centrifugation was conducted for 10 min at 1200 rpm, a supernatant was taken as a test solution that is injected via nanoliter liquid separation, and the primary mass spectrum and the secondary mass spectrum were collected by using a high resolution mass spectrum.

4. Screening and Confirmation with Database Searching

Figure 1:
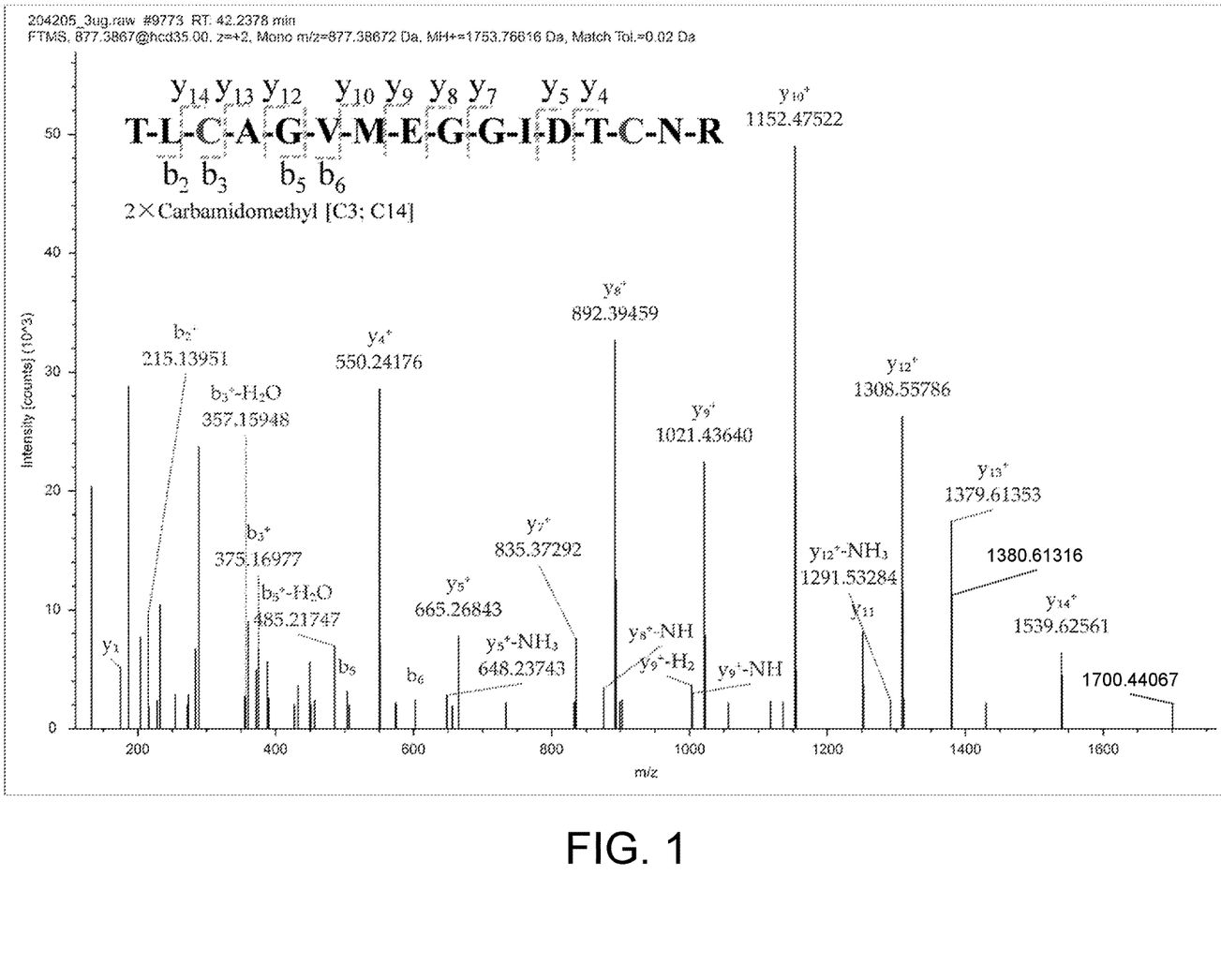
FIG. 1 shows a tandem mass spectrogram spectra of marker peptide of snake venom thrombin-like enzymes from *Agkistrodon Halys Pallas*.
Figure 2:
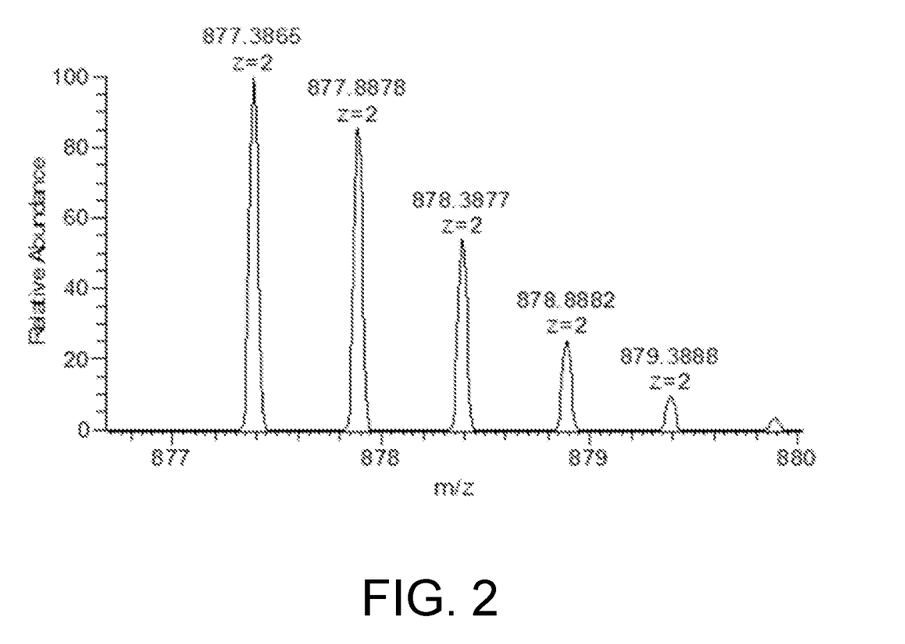
FIG. 2 shows a mass spectrogram spectra of marker peptide of snake venom thrombin-like enzymes from *Agkistrodon Halys Pallas*.

NCBI and UniProt were applied to integrate the relevant snack protein library and venom protein library, and then a snack and venom database was established. Based on a Peptidemass function provided by the UniProt, results of enzymatically hydrolysing SVTLEs proteins of different species with the trypsin was simulated, a sequence of the marker polypeptide of *Agkistrodon Halys Pallas* relative to other species was obtained by comparing a protein sequence of thrombin-like enzyme from *Agkistrodon Halys Pallas* with that in other species, a mass spectrum database was searched by using Proteome Discoverer Software (Version 2.2), and "TLCAGVMEGGIDTCNR" was confirmed as the marker peptide of the SVTLEs from *Agkistrodon Halys Pallas* by referring to the principles of (1) 8-25 amino acid; (2) avoiding peptide fragments artificially modified easily as much as possible; and (3) no omission of restriction site in digestion, etc. According to the detection result, the molecular weight and the secondary mass spectrum of marker peptide are in consistence with theoretical values, as shown in FIG. 1 and FIG. 2.

Embodiment 2

SVTLEs from *Agkistrodon Halys Pallas* in multiple-reaction monitoring (MRM) qualitative and quantitative analysis samples.

1. Instrument and Equipment

SCIEX Triple Quad 6500 Mass Spectrometer, CP225D Electronic Scales (Sartorius, Germany), Sigma 3-30 K Refrigerated Centrifuger (Sigma, Germany), Milli-QAdvantage A10 UP Water Purification System (Millipore, America).

2. LC-MS Conditions

Liquid phase conditions: Waters ACQUITY UPLC BEH $C_{18}$ chromatographic column (50 mm×2.1 mm, 1.7 μm); column temperature: 40° C.; sample size: 2 μL; flow rate: 0.2 mL/min; 0.1% formic acid solution and 0.1% formic acid acetonitrile as mobile phase A, and B respectively for gradient elution, wherein the elution procedure is as follows: 0-1 min, mobile phase A 80%; 1→5 min, mobile phase A 80%→100%; 5→7 min, mobile phase A 10%→10%.

Mass spectrum conditions: ESI source, positive ion scanning mode, multi-reaction monitoring; regard mass-to-charge ratio (m/z) 877.4 (double-charge)→892.4 as the quantitative iron pair, while m/z 877.4 (double-charge) →550.2 as the qualitative ion pair; vortex ion spraying temperature: 500° C.; ionization voltage: 5.5 kV; outlet voltage of a collision chamber: 10 V; inlet voltage EP: 10 V; collision energy (CE): 45 V, declustering potential (DP): 135 V.

3. Solution Preparation 3.1 Preparation of Reference Solutions 10 mg of reference substance of the marker peptide screened in Embodiment 1 was precisely weighed, put it in a 100 mL measuring flask, dissolved with 25 mmol/L ammonium bicarbonate solution and diluted to the scale, uniform mixing was conducted, 0.1 mL, 0.25 mL, 0.5 mL, 1 mL, 2 mL of mixtures were precisely weighed, put in 100 mL measuring flasks respectively and diluted with the 25 mmol/L ammonium bicarbonate solution to the scale, and uniform mixing was conducted; and 10 μL of 0.2 mol/L dithiothreitol solution was added in 200 μL of a mixture, uniform mixing was conducted for reaction for 1 h at 60° C., 20 μL of a 0.2 mol/L iodoacetamide solution was added in another 200 μL of a mixture, a product was put in the dark for 30 min, 760 μL of the 25 mmol/L ammonium bicarbonate solution and 10 μL of a 0.4 mg/mL trypsin solution were added in another 200 μL of mixtures for reaction for 90 min at 37° C. and inactivation for 10 min at 90° C. respectively, then cooled to the room temperature, centrifugation was conducted for 10 min at 1200 rpm, and a supernatant was taken as a series of standard solution for the reference substance.

3.2 Preparation of Test Solution 20 mg of to-be-detected sample was put in a 10 mL measuring flask and dissolved with a 25 mmol/L ammonium bicarbonate solution to a constant volume; 200 μL of the solution was precisely measured, 10 μL of a 0.2 mol/L dithiothreitol solution was added, a mixture was blended uniformly and reacted for 1 h at 60° C., 20 μL of a 0.2 mol/L iodoacetamide solution was added, a mixture was put in the dark for 30 min, 760 μL of the 25 mmol/L ammonium bicarbonate solution and 10 μL of a 0.4 mg/mL trypsin solution (which was newly prepared upon use) were added, the mixture was reacted for 90 min at 37° C. and inactivated for 10 min at 90° C., then cooled to the room temperature, centrifugation was conducted for 10 min at 1200 rpm, and a supernatant was taken as a test solution.

3.3 Preparation of Blank Solution

200 μL of a 25 mmol/L ammonium bicarbonate solution was precisely weighed, 10 μL of a 0.2 mol/L dithiothreitol solution was added for uniform mixing, reaction was conducted for 1 h at 60° C., 20 μL of a 0.2 mol/L iodoacetamide solution was added, a mixture was put in the dark for 30 min, 760 μL of the 25 mmol/L ammonium bicarbonate solution and 10 μL of a 0.4 mg/mL trypsin solution (which was newly prepared upon use) were added, the mixture was reacted for 90 min at 37° C. and inactivated for 10 min at 90° C., then cooled to the room temperature, centrifugation was conducted for 10 min at 1200 rpm, and a supernatant was taken as a blank solution.

4. Determining Method

2 μL of a to-be-detected solution was taken and detected according to the LC-MS conditions specified in Item 2, a linear regression equation (r>0.99) was calculated with the concentration of marker peptide in the series of standard reference solutions as a horizontal coordinate and a corresponding peak area as a vertical coordinate, the concentration of test solution was calculated through the regression equation, and then the content of thrombin-like enzyme in the to-be-detected sample was calculated.

5. Specificity

2 μL of the test solution, 2 μL of the blank solution and 2 μL of the reference solution were taken respectively for liquid quality analysis, and results showed that, the blank solution had no interference peak at the position that a peak appeared of the reference solution, while the test solution had a responded chromatographic peak at the position that a peak appeared of the reference solution, indicating that the method was good in specificity, as shown in FIG. 1.

6. Limit of Detection (LOD) and Limit of Quantification (LOQ)

Figure 3:
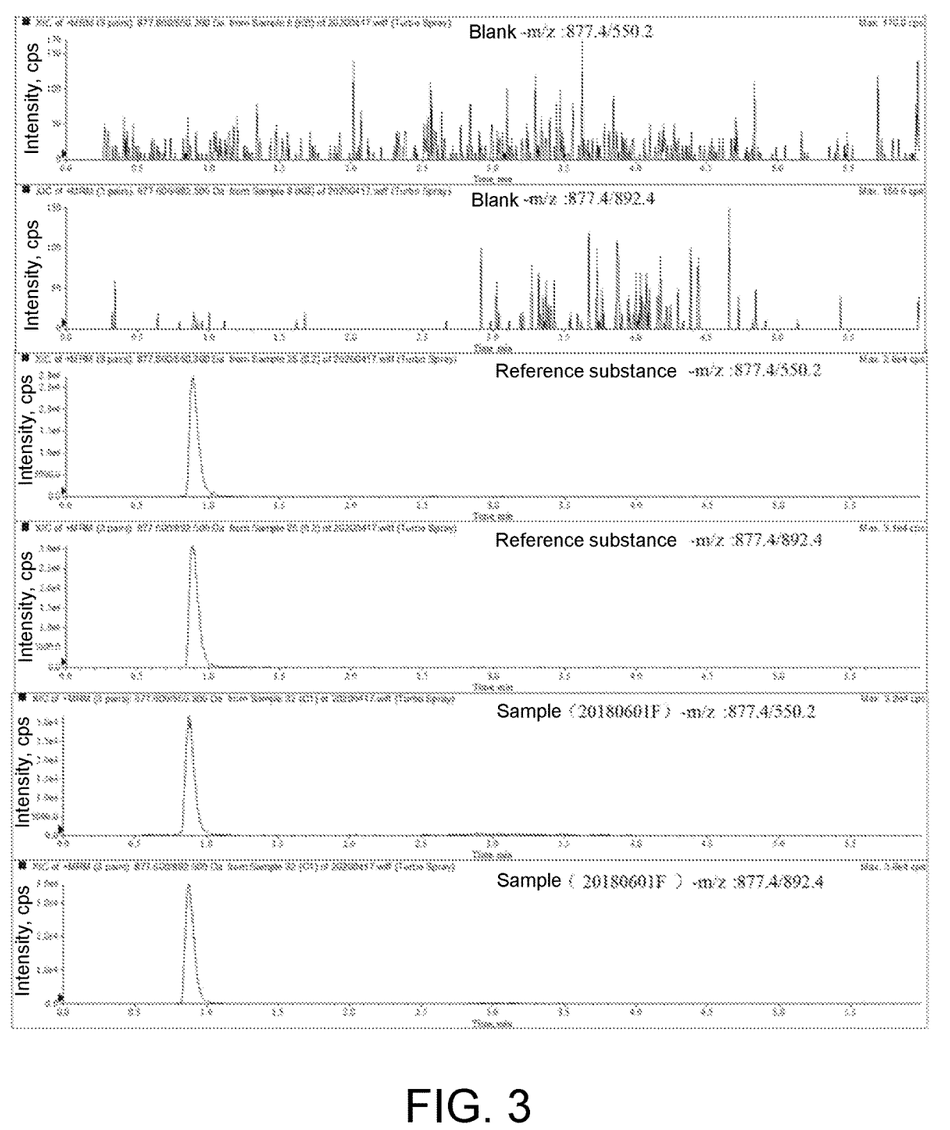
FIG. 3 shows an investigation of specificity map.
Figure 4:
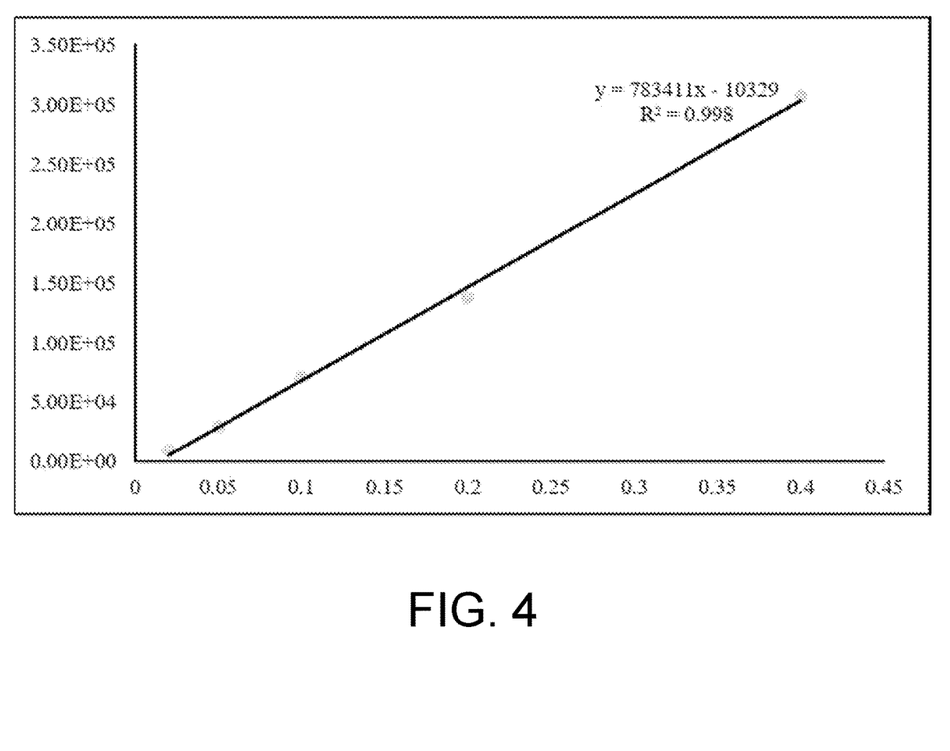
FIG. 4 shows a linearity and range map.
Figure 5:
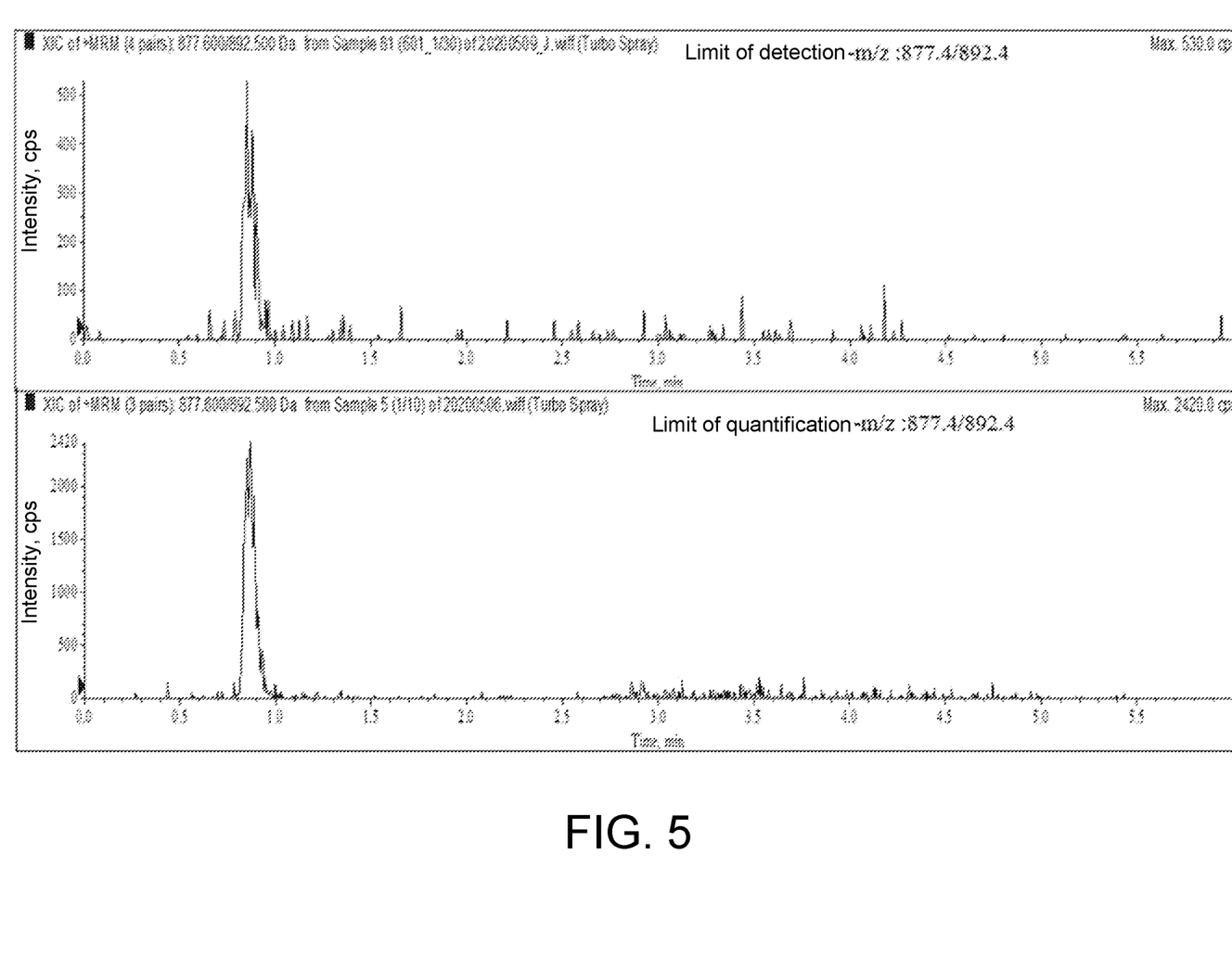
FIG. 5 shows a map for a limit of detection and a limit of quantification.

0.02 μg/mL reference solution was diluted with water to prepare 6 ng/mL and 2 ng/mL reference solutions, 2 μL of the reference solutions were injected into an effective liquid chromatograph-mass spectrometer, and 877.4 (double-charge)→892.4 was taken as the quantitative ions for detection. When a concentration of the reference solution is 2 ng/mL, a signal-to-noise ratio for the quantitative ion pair of the marker peptide is 3.4, but when the concentration is 6 ng/mL, the signal-to-noise ratio is 11.8. Thus, the limit of detection and the limit of quantification are 2 ng/mL and 6 ng/mL respectively, as shown in FIG. 3.

7. Linearity and Range

A series of reference standard solutions with final concentrations of 0.02 μg/mL, 0.05 μg/mL, 0.1 μg/mL, 0.2 μg/mL, 0.4 μg/mL were taken in Item 3.1, and 877.4 (double-charge)→892.4 was used as the quantitative ion pair for detection. A linear regression equation: y=783411x−10329 ($R^2$=0.998) was calculated with the concentration of marker peptide in the series of reference standard solutions as a horizontal coordinate and a corresponding peak area as a vertical coordinate, and within a range from 0.02 μg/mL to 0.4 μg/mL, the concentration of marker peptide is in linear relation with a chromatographic peak area, as shown in FIG. 2.

8. Repeatability 6 solutions were prepared in parallel according to the method for preparing the test solution, analyzed and then detected by using 877.4 (double-charge)→892.4 as the quantitative ion pair. According to results of six parallel tests, the RSD content is 2.20%, and the method is excellent in repeatability.

TABLE 2

| No. | Sample Volume (mg) | Concentration (μg/mL) | Content (μg/mg) |
|---|---|---|---|
| 1 | 10.05 | 0.22 | 0.53 |
| 2 | 10.27 | 0.21 | 0.52 |
| 3 | 9.90 | 0.22 | 0.55 |
| 4 | 10.31 | 0.22 | 0.52 |
| 5 | 10.05 | 0.21 | 0.53 |
| 6 | 9.98 | 0.21 | 0.53 |
| Mean Value | / | / | 0.53 |
| RSD | / | / | 2.2% |

9. Precision

The test solution was injected for 6 times successively, and the peak area was measured by using 877.4 (double-charge)→892.4 as the quantitative ion pair, which showed that RSD was 2.6%, and the instrument is high in precision.

TABLE 3

| No. | Peak Area | Mean Value | RSD |
|---|---|---|---|
| 1 | 159000 | 159167 | 2.6% |
| 2 | 159000 | | |
| 3 | 162000 | | |
| 4 | 152000 | | |
| 5 | 159000 | | |
| 6 | 164000 | | |

10. Stability

The test solution was treated and then placed at 8° C., and determination with sample injection was conducted at 0, 2, 4, 6, 8, 16 and 24 h respectively, and the peak area RSD was determined to be 3.0% by using 877.4 (double-charge)→892.4 as the quantitative ion pair, indicating that the marker peptide in the test solution was stable within 24 h at 8° C.

TABLE 4

| Time (h) | Peak Area | Mean Value | RSD |
|---|---|---|---|
| 0 | 143000 | 155500 | 3.0 |
| 2 | 149000 | | |
| 4 | 155000 | | |
| 6 | 154000 | | |
| 8 | 156000 | | |
| 16 | 156000 | | |
| 24 | 163000 | | |

11. Recovery 19.80 mg of venom samples with a known content of marker peptide (with content of 0.53 μg/mg) was precisely weighed, dissolved with a 25 mmol/L ammonium bicarbonate solution and diluted to 10 mL; suitable quantity of reference solutions of the marker peptide were added in 200 μL of products in 9 copies respectively, a recovery rate investigation solution was prepared according to Item 3.2, and detection was conduction with 877.4 (double-charge) →892.4 as the quantitative ion pair. A result showed that the recovery rates were all within a range from 91.18% to 107.84% at three levels, the average recovery rate was 96.23%, RSD was 6.600, and this method is high in recovery rate.

TABLE 5

| No. | Content in sample (ng) | Addition quantity (ng) | Measured Value (ng) | Recovery Rate | Mean Value | RSD |
|---|---|---|---|---|---|---|
| 1 | 104.94 | 31 | 133 | 93.53% | 96.23% | 6.6% |
| 2 |  |  | 136 | 103.53% |  |  |
| 3 |  |  | 134 | 96.87% |  |  |
| 4 |  | 62 | 165 | 100.10% |  |  |
| 5 |  |  | 160 | 91.77% |  |  |
| 6 |  |  | 160 | 90.10% |  |  |
| 7 |  | 93 | 187 | 91.18% |  |  |
| 8 |  |  | 187 | 91.18% |  |  |
| 9 |  |  | 200 | 107.84% |  |  |

12. Sample Testing

The venom samples marked as the venom of *Agkistrodon Halys Pallas* (20180601F, 20180702F, 20170802), the venom of *Bothrops atrox* (U.S. Pat. Nos. 2,004,171, 2,004,172, 2,004,173, 2,004,174) and the venom of two batches of unknown snake species (20200304, 20200405) were detection according to the method specified in Item 3 and 4.

12.1 Qualitative Analysis

According to the pretreatment method and the analysis method for a snake venom sample, a detection result showed that, in the ion flow chromatography of the test solution extracted with 877.4 (double-charge)→550.2 and 877.4 (double-charge-→892.4 ion pairs (in mass-to-charge ratio (m/z)), these three batches of venom samples of *Agkistrodon Halys Pallas* had chromatographic peaks with the chromatographic retention times consistent with that of the reference marker peptide (0.88 min), while no chromatographic peak is extracted at the chromatographic retention time of the reference marker peptide for four batches of samples marked as the venom of *Bothrops atrox* and two batches of samples marked as the venom of unknown snake species. Thus, the marker peptide TLCAGVMEGGIDTCNR may be detected in the three batches of samples marked as the venom of *Agkistrodon Halys Pallas*, and the source could be confirmed as *Agkistrodon Halys Pallas*. Since such marker peptide was not detected in four batches of samples marked as the venom of *Bothrops atrox* and two batches of samples marked as the venom of unknown snake species, it can be confirmed that these 6 batches of venoms are not originated from *Agkistrodon Halys Pallas*.

12.2 Quantitative Analysis

As for samples detected with the marker peptide (TLCAGVMEGGIDTCNR), the concentration of the test solution was calculated through the regression equation, and then a content of thrombin-like enzyme in the sample was calculated. A result is as shown in Table 6. Contents of crude venom in three batches were all higher than 0.4 μg/mg. Thus, this method may be used to detect the content of thrombin-like enzyme for *Agkistrodon Halys Pallas* in the sample.

TABLE 6

| Batch No. | Content (μg/mg) |
|---|---|
| 20180601F | 0.53 |
| 20180702F | 0.52 |
| 20170802 | 0.47 |

The above embodiments are preferred implementations of the present invention, but the implementations of the present invention are not limited by the embodiments. Any other changes, modifications, combinations, replacement and simplification made in accordance with the essential spirit and principle of the present invention shall be considered as an equivalent mode of replacement, and are included in the protection range of the present invention.

What is claimed is:

1. A marker peptide of snake venom thrombin-like enzymes (SVTLEs) from *Agkistrodon Halys Pallas*, wherein an amino acid sequence of the marker peptide is TLCAGVMEGGIDTCNR.

2. A method for detecting a source of species and/or a content of the SVTLEs in a to-be-detected sample by using the marker peptide according to claim 1, comprising the following steps of:
   (1) pretreating the to-be-detected sample by trypsin through enzymolysis, and taking a supernatant of an enzymolysis liquid as a test solution;
   (2) pretreating a reference substance of the marker peptide of snake venom from *Agkistrodon Halys Pallas* by the trypsin through enzymolysis, and preparing a series of reference solutions with different concentrations;
   (3) injecting the test solution in the step (1) and the reference solution in the step (2) into a liquid chromatography-mass spectrometer, conducting multiple-reaction monitoring by employing an electrospray positive ion mode with double charges 877.4→550.2 (in mass to charge (m/z) ratio) as a qualitative ion pair and double charges 877.4→892.4 as a quantitative ion pair, wherein a liquid phase conditions are as follows: $C_{18}$ a chromatographic column has a size of 50 mm×2.1 mm (1.7 μm particle size), a column temperature is 40° C., a sample size is 2 μL, a flow rate is 0.2 mL/min, a mobile phase A is 0.1% formic acid solution, and a mobile phase B is 0.1% formic acid acetonitrile for gradient elution, wherein a elution program is as follows: 0 min, the mobile phase A: 80%; 1→5 min, the mobile phase A 80%→10%; and 5→7 min, the mobile phase A 10%→10%;

(4) in an extracted test solution extracted ion chromatograms (XIC) of the qualitative ion pair and the quantitative ion pair in the step (3), if showing a chromatographic peak with a chromatographic retention time of the to-be-detected sample is consistent with that of the marker peptide, showing that the to-be-detected sample includes the amino acid sequence of TLCAGVMEG-GIDTCNR, proving that the to-be-detected sample is originated from *Agkistrodon Halys Pallas*, or otherwise proving that the to-be-detected sample is not originated from *Agkistrodon Halys Pallas*; and (5) extracting the double-charge 877.4→892.4 chromatogram of the quantitative ion pair, calculating a linear regression equation with a concentration of the marker peptide in the series of reference solutions as a horizontal coordinate and a corresponding peak area as a vertical coordinate (r>0.99), calculating a concentration of the test solution through the regression equation, and then calculating a content of thrombin-like enzyme in the to-be-detected sample.

3. The method according to claim 2, wherein a limit of detection for the marker peptide of the snake venom from *Agkistrodon Halys Pallas* is 2 ng/mL, while a limit of quantification is 6 ng/mL.

4. The method according to claim 2, wherein the pretreating with the trypsin through enzymolysis in the step (1) comprises the following specific operation steps: putting 20 mg of the to-be-detected sample in a 10 mL measuring flask, dissolving the to-be-detected sample with 25 mmol/L ammonium bicarbonate solution to a constant volume; and measuring 200 μL of a product, adding 10 μL of a 0.2 mol/L dithiothreitol solution, conducting uniform mixing, conducting reaction for 60 min at 60° C., adding 20 μL of a 0.2 mol/L iodoacetamide solution, conducting reaction in dark for 30 min, adding 760 μL of a 25 mmol/L ammonium bicarbonate solution and 10 μL of a 0.4 mg/mL trypsin solution for enzymolysis for 90 min at 37° C., conducting inactivation for 10 min at 90° C., cooling to a room temperature, and conducting centrifugation for 10 min at 1200 rpm to obtain the supernatant.

5. The method according to claim 2, wherein the pretreating with the trypsin through enzymolysis in the step (2) comprises the following specific operation steps: precisely weighing 10 mg of the reference substance of the marker peptide, putting the reference substance of the marker peptide in a 100 mL measuring flask, dissolving the reference substance of the marker peptide with 25 mmol/L ammonium bicarbonate solution, diluting the reference substance of the marker peptide to a scale, conducting uniform shaking, precisely weighing 0.1 mL, 0.25 mL, 0.5 mL, 1 mL, 2 mL of a mixture to be put in 100 mL measuring flasks respectively, dissolving the mixtures with the 25 mmol/L ammonium bicarbonate solution, diluting the mixtures to the scale, and conducting uniform shaking; and adding 10 μL of a 0.2 mol/L dithiothreitol solution in 200 μL of a product, conducting uniform mixing for reaction for 60 min at 60° C., adding 20 μL of a 0.2 mol/L iodoacetamide solution in another 200 μL of the product for reaction for 30 min in the dark, adding 760 μL of the 25 mmol/L ammonium bicarbonate solution and 10 μL of a 0.4 mg/mL trypsin solution in another 200 μL of the products for enzymolysis for 90 min at 37° C. and inactivation for 10 min at 90° C. respectively, cooling to the room temperature, and conducting centrifugation for 10 min at 1200 rpm to obtain supernatants.

6. The method according to claim 2, wherein a detection conditions about the mass spectrum of the liquid chromatography-mass spectrometer are as follows:

mass spectrum conditions: ESI source, positive ion scanning mode, multiple-reaction monitoring; vortex ion spraying temperature: 500° C.; ionization voltage: 5.5 kV; outlet voltage of the collision chamber: 10 V; inlet voltage EP: 10 V; collision energy CE: 45 V, declustering potential DP: 135 V.

7. The method according to claim 2, wherein the to-be-detected sample is the snake venom.

8. The method according to claim 3, wherein the to-be-detected sample is the snake venom.

9. The method according to claim 4, wherein the to-be-detected sample is the snake venom.

10. The method according to claim 5, wherein the to-be-detected sample is the snake venom.

11. The method according to claim 6, wherein the to-be-detected sample is the snake venom.

* * * * *

SEQUENCE LISTING

```
<160> NUMBER OF SEQ ID NOS: 1

<210> SEQ ID NO 1
<211> LENGTH: 16
<212> TYPE: PRT
<213> ORGANISM: Gloydius ussuriensis

<400> SEQUENCE: 1

Thr Leu Cys Ala Gly Val Met Glu Gly Gly Ile Asp Thr Cys Asn Arg
1               5                   10                  15
```